United States Patent [19]
Bays et al.

[11] Patent Number: 5,707,383
[45] Date of Patent: Jan. 13, 1998

[54] METHOD OF REMOVING SOFT TISSUE IN THE MIDDLE EAR

[75] Inventors: F. Barry Bays; Dan H. Treace, both of Clearwater, Fla.

[73] Assignee: Xomed Surgical Products, Inc., Jacksonville, Fla.

[21] Appl. No.: 539,390

[22] Filed: Oct. 5, 1995

[51] Int. Cl.$^6$ .................................................. A61B 17/32
[52] U.S. Cl. ........................ 606/180; 606/159; 128/898
[58] Field of Search ........................... 606/159, 170, 606/180; 128/898

[56] References Cited

U.S. PATENT DOCUMENTS

| | | | |
|---|---|---|---|
| 2,712,823 | 7/1955 | Kurtin. | |
| 2,867,214 | 1/1959 | Wilson. | |
| 4,459,987 | 7/1984 | Pangburn. | |
| 4,646,736 | 3/1987 | Auth | 606/159 |
| 4,681,106 | 7/1987 | Kensey et al. | 606/180 |
| 4,917,085 | 4/1990 | Smith | 606/159 |
| 5,100,424 | 3/1992 | Jang et al. | 606/159 |
| 5,102,415 | 4/1992 | Guenther et al. | 606/159 |
| 5,192,290 | 3/1993 | Hilal | 606/159 |
| 5,320,634 | 6/1994 | Vigil et al. | 606/159 |
| 5,507,761 | 4/1996 | Duer | 606/159 |

*Primary Examiner*—Michael Buiz
*Assistant Examiner*—Patrick W. Rasche

[57] ABSTRACT

A surgical abrading instrument for removing soft bodily tissue includes a stiffening support member and an abrasive member formed of a rubbery polymeric material. The abrasive member is mounted on the stiffening support member and includes an integral abrasive surface having a roughness to remove soft bodily tissue when the abrasive member is driven against the tissue via movement of the stiffening support member. The abrasive member can be of integral one-piece construction, in which case the abrasive member can also be formed simultaneously with attachment to the stiffening support member. In one embodiment, the stiffening support member includes a cylindrical shaft with proximal and distal ends, and the abrasive member is formed at the distal end of the shaft for rotation about a longitudinal axis thereof.

4 Claims, 1 Drawing Sheet

METHOD OF REMOVING SOFT TISSUE IN THE MIDDLE EAR

BACKGROUND OF THE INVENTION

1. Field of the Invention

The present invention relates to surgical instruments and, more particularly, to surgical abrading instruments for use in cutting and removing soft bodily tissue such as cholesteatomas.

2. Discussion of the Prior Art

Eustachian tube obstruction, rupture of the tympanic membrane during acute otitis media, and hyperactivity of the basal layer of the epidermis of the pars flaccida due to inflammation of the middle ear can sometimes result in formation of a cholesteatoma, that is, a condition whereby stratified squamous epithelium (i.e., skin cells) proliferate within the middle ear. The stratified squamous epithelium of a cholesteatoma desquamates in the middle ear, and the desquamated epithelial debris accumulates in expanding concentric layers that can destroy bone tissue, such as the tympanic ossicles of the ear, and can also serve as a culture medium for microorganisms, resulting in persistent middle ear infection.

Cholesteatomas require surgical removal either through the tympanic membrane of the ear or by mastoidectomy, that is, excision of the mastoid bone behind the ear together with the cholesteatoma. In the past, surgical instruments with abrasive tips, such as fine grit diamond burrs, have been used to remove the desquamated epithelial debris associated with a cholesteatoma; however, such abrasive tips have the disadvantage of being hard and overly traumatic, thereby increasing the risk of injuring the tympanic ossicles of the middle ear and surrounding bony structures.

In fact, surgical abrading instruments with hard abrasive tips are disadvantageous when used in removing any type of soft tissue from the ear and other parts of the body since the hard abrasive tips of such instruments have the capability of gouging or digging into surrounding tissue and organ structures irrespective of whether the surrounding structures are hard or soft. Furthermore, many hard abrasive tips are formed with abrasive particles embedded in a bonding material, thereby increasing the risk of the particles becoming dislodged from the tips and decreasing instrument life and performance.

SUMMARY OF THE INVENTION

Accordingly, it is a primary object of the present invention to overcome the above-mentioned problems and disadvantages of the prior art and to improve surgical abrading instruments for removing soft bodily tissue.

It is another object of the present invention to minimize the likelihood of gouging adjacent tissue structures when removing soft bodily tissue using a surgical abrading instrument.

It is a further object of the present invention to reduce or eliminate the likelihood of abrasive particles being deposited at a surgical site when removing soft tissue from the body using a surgical abrading instrument.

Some of the advantages of the present invention over the prior art are that the surgical abrading instrument permits aggressive removal of soft tissue with less trauma to surrounding tissue, that the surgical abrading instrument can be operated using any type of medical instrument handle or motorized handpiece, that the surface roughness or abrasiveness of the surgical abrading instrument can be tailored for specific types of tissue, that the physical characteristics of the surgical abrading instrument are highly reproducible and that relatively inexpensive polymeric materials can be used in fabricating the surgical abrading instrument to reduce cost.

The present invention is generally characterized in a surgical abrading instrument including a stiffening support member and an abrasive member formed of a rubbery polymeric material. The abrasive member is mounted on the stiffening support member and includes an integral abrasive surface with a roughness to remove soft bodily tissue when the abrasive member is driven against the tissue via movement of the stiffening support member. In a preferred embodiment, the abrasive member is of integral one-piece construction and the rubbery polymeric material has a hardness of between about 20 and about 70 durometer on the Shore A scale and a surface roughness of between about 160 and about 180 according to N.T.M.A. Mold Cavity Finish Guidelines.

Another aspect of the present invention is generally characterized in a method of removing soft bodily tissue including the steps of positioning an abrasive member formed of a rubbery polymeric material with an integral abrasive surface adjacent the soft bodily tissue and moving the abrasive member against the soft bodily tissue. In one embodiment, the positioning step includes positioning the abrasive member adjacent a cholesteatoma.

Other objects and advantages of the present invention will become apparent from the following description of the preferred embodiments taken in conjunction with the accompanying drawings, wherein like parts in each of the several figures are identified by the same reference characters.

DETAILED DESCRIPTION OF THE PREFERRED EMBODIMENTS

Figure 1:
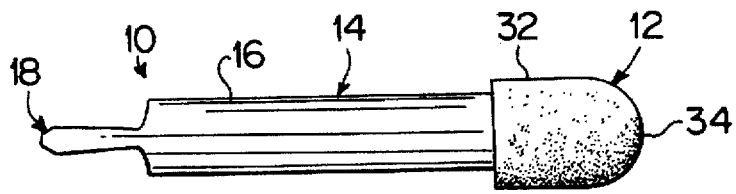
FIG. 1 is a side elevational view of the surgical abrading instrument according to the present invention.
Figure 2:
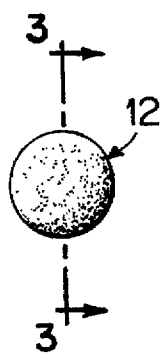
FIG. 2 is a front elevational view of the surgical abrading instrument of FIG. 1.
Figure 3:
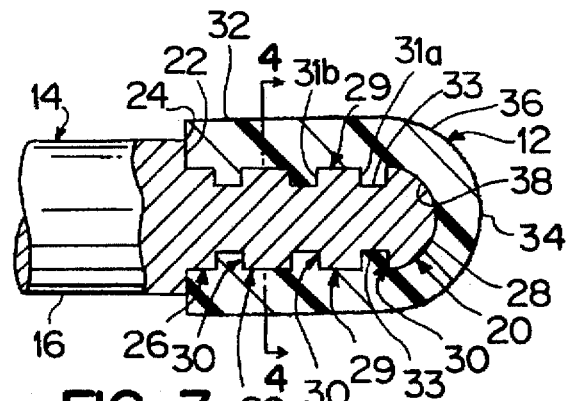
FIG. 3 is a fragmentary sectional view taken through line 3—3 in FIG. 2.
Figure 4:
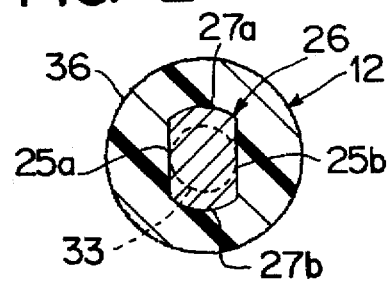
FIG. 4 is a sectional view taken through line 4—4 in FIG. 3.

The surgical abrading instrument of the present invention is described hereinafter as an instrument for cutting and removing the stratified squamous epithelium that lines the middle ear when a cholesteatoma occurs. It will be appreciated, however, that the surgical abrading instrument of the present invention can be used to perform soft cutting and removal of any type of soft tissue of the body without gouging or digging into adjacent tissue or organ structures.

A surgical abrading instrument 10 according to the present invention, as illustrated in FIGS. 1–4, includes an abrasive member 12 mounted on a stiffening support member 14. Support member 14 has a configuration similar to a bur blank and includes a cylindrical shaft or body 16 having a proximal end 18 and a distal end 20. Proximal end 18 of the shaft is notched on opposite sides to fit a motorized handpiece, such as the REDI-BUR handpiece distributed by TreBay Medical Corporation of Clearwater, Fla., but can have any configuration to fit available motorized handpieces or medical instrument handles. Distal end 20 includes a shoulder 22 connecting a circular edge 24 of the shaft with a neck 26 of generally cylindrical configuration with truncated sides 25a and 25b, the truncated sides defining a pair of flat surfaces on opposite sides of the generally cylindrical neck in parallel relation to each other and a longitudinal axis of the shaft. Cylindrical surfaces 27a and 27b of the neck are connected by sides 25a and 25b and are of smaller diameter than the circular edge. Neck 26 terminates distally at a rounded tip 28 and includes a plurality of longitudinally spaced ribs 29 separated by undercuts or annular grooves 30, each rib being generally rectangular in cross-section with front and rear faces 31a and 31b oriented perpendicular to the longitudinal axis of the shaft and a bottom 33 of each groove.

Abrasive member 12 is preferably of integral one-piece construction and includes a hollow cylindrical portion 32 with a rounded tip 34, the cylindrical portion 32 abutting shoulder 22 and having an outer diameter greater than the diameter of circular edge 24. In addition, rounded tip 34 of the abrasive member has an outer radius greater than the radius of the rounded tip 28 of the cylindrical neck so that an exterior surface 36 of the abrasive member protrudes radially outward of the shaft and distally beyond the neck. The exterior surface 36 has a surface roughness or abrasiveness to define an integral abrasive surface to aggressively cut soft bodily tissue, such as cholesteatomas. Interior surface 38 of the abrasive member conforms substantially to the shape of neck 26 and is thus interlocked with the ribs 29 formed on the neck and the flat surfaces defined by truncated sides 25a and 25b thereof to prevent the abrasive member from axially or rotatably moving or slipping relative to the shaft.

The abrasive member 12 is made of a rubbery polymeric material formed to have a surface roughness to aggressively cut soft bodily tissue, such as cholesteatomas, and a resilience or hardness to provide a cushioning effect that prevents the abrasive member from gouging adjacent tissue and organ structures as the soft bodily tissue is being cut. To this end, the polymeric material is preferably an elastomer with a hardness of between about 20 and about 70 durometer on the Shore A, one-second, scale for plastics, and a surface roughness of between about 160 and about 180 according to the National Tooling & Machining Association (N.T.M.A.) Mold Finish Guidelines. In a preferred embodiment, the polymeric material is an elastomer having a hardness of about 35 durometer on the Shore A scale. Some examples of polymeric materials that can be used in forming the abrasive member include C-FLEX, silicone, natural or synthetic rubber and other thermosetting and thermoplastic elastomers.

In forming the surgical abrading instrument 10, any conventional method can be used. A preferred manner of forming the surgical abrading instrument 10 is by molding the abrasive member 12 with the shaft 16 positioned in the mold such that the abrasive member is formed simultaneously with attachment to the shaft. One method uses a mold having two parts which, when joined together, form a first cavity or recess having the exterior shape of the abrasive member 12 and a second cavity or recess having the shape of the shaft 16. The surface of the first cavity is finished to have a uniform surface roughness corresponding to the desired surface roughness of the abrasive member, for example by machining, sandblasting, EDM (electrical discharge machining) or by chemically treating (i.e., etching) the surface of the first cavity. The N.T.M.A. mold cavity finish guidelines demonstrate a 160 finish using a vapor blast at 90 p.s.i. with 60 grit silica sand at 5 inches and a 180 finish is demonstrated using a coarse sand blast with 24 mesh aluminum oxide.

Shaft 16 is placed in the second cavity of the mold so as to position the neck 26 within the first cavity of the mold, after which the polymeric material is injected into the mold via an access port and made to flow into the first cavity between the neck and the roughened surface of the first cavity to form the abrasive member 12. The polymeric material is then cured in accordance with the manufacturer's recommendations to produce the finished part.

In a preferred embodiment, particularly suited to cholesteatoma surgery, exterior surface 36 of abrasive member 12 has a diameter of between about 0.08 and 0.10 inches, cylindrical shaft 16 has a diameter of about 0.0625 inches, neck 26 has a diameter of about 0.035 inches and ribs 29 have a diameter of about 0.050 inches.

In use, the surgical abrading instrument 10 can be mounted on a motorized handpiece to be mechanically driven or on a medical instrument handle to be moved manually using only hand motions. The proximal end 18 shown in FIG. 1 is configured to be held in compression between tensioned jaws of a collet, such as the collet used in the aforementioned REDI-BUR handpiece; however, the proximal end can have any configuration to fit available motorized handpieces and medical instrument handles including, but not limited to, configurations where the proximal end is formed with a handle as an integral one-piece unit. When it is desired to cut and remove soft tissue from the body, the surgical abrading instrument 10 is positioned to locate abrasive member 12 adjacent the tissue, for example by manipulating the handpiece or handle on which the surgical abrading instrument is mounted. The abrasive member of the surgical abrading instrument is then brought into contact with the tissue and moved relative to the tissue to frictionally engage, softly cut and remove the tissue. The movement, for example, can be a single wiping or dabbing motion, continuous or intermittent rotation about the longitudinal axis of the surgical abrading instrument, reciprocating axial movement or vibration. Movement is imparted to the abrasive member 12 via the shaft 16, and the abrasive member is prevented from slipping relative to the shaft by engagement of the interior surface 38 of the abrasive member with truncated sides 25a and 25b and the ribs 29 formed on the neck 26 at the distal end of the shaft 16. If, when removing the soft tissue, the abrasive member contacts tougher tissue, such as bony structures, the resilience of the soft polymer material will help prevent the tougher tissue from being gouged or otherwise damaged.

Figure 5:
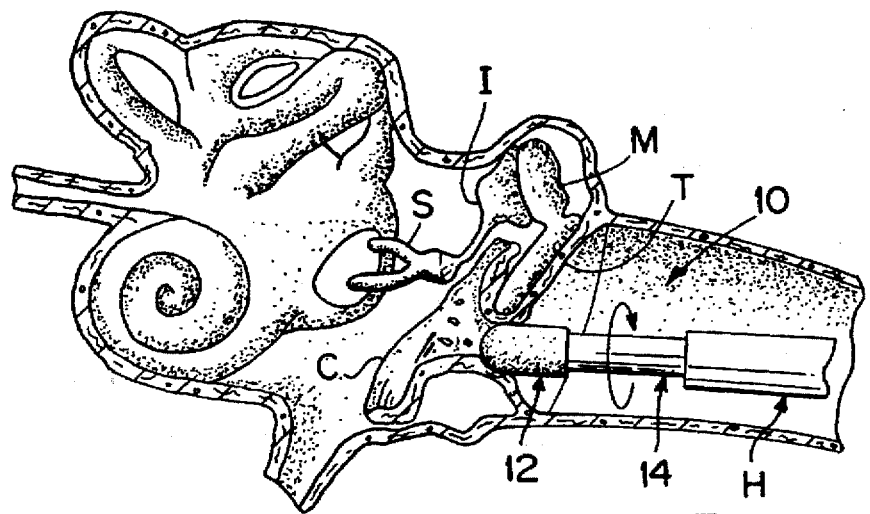
FIG. 5 is a diagram of the middle ear illustrating use of the surgical abrading instrument of the present invention to remove a cholesteatoma.

As mentioned above, the surgical abrading instrument 10 of the present invention is particularly useful in clearing the epithelial debris associated with cholesteatomas. FIG. 5 is a diagram of the middle ear showing the surgical abrading instrument 10 being inserted through the tympanic membrane T to position the abrasive member 12 adjacent a cholesteatoma C. Alternatively, the surgical abrading instrument 10 could be inserted into the ear via excision of the mastoid process (not shown) as part of a mastoidectomy aimed at removing the cholesteatoma. The surgical abrading instrument 10 is shown mounted at the end of a motorized handpiece H which rotates the surgical abrading instrument about the longitudinal axis of the shaft 16 at speeds suitable for removing the cholesteatoma (e.g., between about 200 and about 20,000 rpm dependent upon the material of the abrasive member and the toughness, consistency and location of the tissue). The rotating abrasive member 12 is brought into contact with the cholesteatoma C in the middle ear so that the integral abrasive surface of the abrasive member engages the cholesteatoma tissue to softly cut and remove the tissue without gouging or digging into surrounding tissue and organ structures such as the tympanic ossicles S, I and M.

Figure 6:
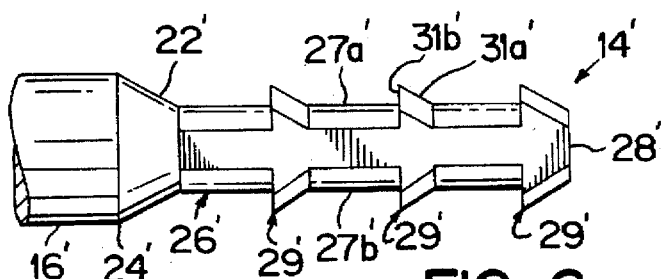
FIG. 6 is a fragmentary side view of a modification of the surgical abrading instrument according to the present invention.

A modification of the stiffening support member for the surgical abrading instrument of the present invention is shown in FIG. 6 wherein the modified stiffening support member 14' is similar to the stiffening support member 14 shown in FIGS. 1–4 but with a frustoconically-shaped shoulder 22' and a plurality of longitudinally-spaced, frustoconically-shaped ribs 29' formed on neck 26'. Shoulder 22' tapers radially inward from circular edge 24' of shaft 16' to neck 26', the neck being of generally cylindrical configuration with truncated sides and a flat distal end 28'. Ribs 29' extend radially outward from cylindrical surfaces 27a' and 27b' of the neck at longitudinally spaced locations, and each of the ribs includes a front face 31a' oriented at an angle relative to a longitudinal axis of the support member and a rear face 31b' oriented perpendicular to the longitudinal axis. Ribs 29' have fewer edges than rectangular ribs 29 such that, when forming the abrasive member, the polymeric material can fill the mold more completely and closely conform to the shape of the neck.

The abrasive member of the surgical abrading instrument 10 can be formed in any shape dependent upon procedural use including spherical, conical and cylindrical shapes with flat, rounded or pointed tips, tapered shapes with rounded or pointed tips, and shapes such as ovals, buds, flames, pears, Henahan drill tips, Shannon cylinders and tapered shapes, Swanson pilot point reamers, wire pass drills, Lindemann bone cutters, and cylindrical and tapered dermabrader shapes. The size of the abrasive member will also vary according to procedural use. For example, in the cholesteatoma surgery described above, the abrasive member must have an outer diameter to fit within the external auditory canal and be maneuverable in the middle ear (e.g., about 0.1 inches).

The surface roughness of the abrasive member will depend upon the consistency and toughness of the tissue to be abraded, the speed of operation of the instrument and the material of which the abrasive member is formed. In addition, the surface roughness can be uniform across the exterior surface of the abrasive member or vary according to location on the exterior surface of the abrasive member.

While the abrasive member is preferably attached to the shaft as it is molded, any suitable means for attaching the abrasive member to the shaft can be used including forming the abrasive member with threads and threading the abrasive member onto the shaft, holding the abrasive member in place with a screw, bonding the abrasive member to the shaft, forming the abrasive member and shaft with mating detents, and holding the abrasive member in place using compression or a collar.

The stiffening support member can be made of any medically acceptable material that is sufficiently rigid to serve as a mandrel or backing upon which the abrasive member can be mounted but is preferably made of stainless steel. While the stiffening support member is shown herein as a cylindrical shaft, it will be appreciated that the support member could be configured as a block, rod or bar or have any other shape to mount and stiffen the soft, polymeric abrasive member. In the case of a block, rod or bar, the abrasive member could also be configured as a pad and mounted on only one side of the support member instead of being formed around the distal end. As mentioned previously, the proximal end of the stiffening support member is configured to fit available motorized handpieces or medical instrument handles and can also form part of an integral one-piece handle if desired.

When the abrasive member is to be molded onto a neck at the distal end of the shaft, the neck can be formed with ribs and/or grooves that are circumferential, helical, longitudinal and/or oriented at any angle relative to the longitudinal axis of the shaft so as to prevent the abrasive member from slipping relative to the shaft. Further, the grooves can be continuous or discontinuous and regularly or irregularly spaced along the neck. The neck can have any configuration to serve as a mandrel around which the abrasive member is formed including, but not limited to, the generally cylindrical configurations shown and described, straight and curved configurations, inwardly or outwardly tapered configurations, configurations with balls or other enlargements at one end or at spaced intervals, and configurations where the neck is of the same diameter or larger diameter than the circular edge of the cylindrical shaft. When the stiffening support member defines a shoulder, the shoulder can be straight, tapered or curved. When the neck is formed with truncated sides, the flat surfaces formed by the truncated sides can have any length or width but preferably extend along the entire length of the neck or substantially the entire length of the neck to prevent rotational slipping of the abrasive member.

From the above, it will be appreciated that the surgical abrading instrument of the present invention can aggressively cut soft bodily tissue without causing trauma to adjacent and surrounding tissue structures by use of an abrasive member made of a rubbery polymeric material formed to have an integral abrasive surface. By "rubbery" is meant having a durometer hardness similar to that of known elastomers such as rubber. The abrasive member of the surgical abrading instrument according to the present invention has an integral abrasive surface which, if of integral one-piece construction, is less expensive to produce than diamond or carbide tip surfaces and is less likely to fragment because it is not necessary to embed particles in the integral abrasive surface which can become dislodged. Under certain circumstances, however, it may be desirable to embed abrasive particles in the rubbery polymeric material to form an integral abrasive surface.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of removing soft bodily tissue in the middle ear comprising the steps of positioning an abrasive member formed of a rubbery polymeric material in the middle ear adjacent the soft bodily tissue, the abrasive member being of integral one-piece construction and having an abrasive surface with a roughness to remove soft bodily tissue when moved against the tissue; and moving the abrasive surface of the abrasive member against the soft bodily tissue.

2. A method of removing soft bodily tissue as recited in claim 1 wherein said moving step includes driving the abrasive member via movement of a stiffening support member upon which the abrasive member is mounted.

3. A method of removing soft bodily tissue as recited in claim 2 wherein said moving step includes rotating said stiffening support member about a longitudinal axis thereof.

4. A method of removing soft bodily tissue as recited in claim 2 wherein said positioning step includes positioning the abrasive member adjacent a cholesteatoma.

* * * * *